(12) United States Patent
Nonaka et al.

(10) Patent No.: US 10,881,881 B2
(45) Date of Patent: Jan. 5, 2021

(54) ROTARY IRRADIATION APPARATUS, ROTARY IRRADIATION METHOD, AND ROTATION RADIOTHERAPY APPARATUS

(71) Applicants: KABUSHIKI KAISHA TOSHIBA, Minato-ku (JP); TOSHIBA ENERGY SYSTEMS & SOLUTIONS CORPORATION, Kawasaki (JP)

(72) Inventors: Tomoyuki Nonaka, Yokohama (JP); Shinya Matsuda, Kamakura (JP); Tomofumi Orikasa, Yokohama (JP)

(73) Assignees: KABUSHIKI KAISHA TOSHIBA, Minato-ku (JP); TOSHIBA ENERGY SYSTEMS & SOLUTIONS CORPORATION, Kawasaki (JP)

(*) Notice: Subject to any disclaimer, the term of this patent is extended or adjusted under 35 U.S.C. 154(b) by 0 days.

(21) Appl. No.: 16/569,332

(22) Filed: Sep. 12, 2019

(65) Prior Publication Data
US 2020/0001119 A1 Jan. 2, 2020

Related U.S. Application Data

(63) Continuation of application No. PCT/JP2018/009686, filed on Mar. 13, 2018.

(30) Foreign Application Priority Data

Mar. 14, 2017 (JP) .................. 2017-048806

(51) Int. Cl.
*A61N 5/10* (2006.01)
*A61N 5/01* (2006.01)
(Continued)

(52) U.S. Cl.
CPC ............ *A61N 5/1081* (2013.01); *A61N 5/01* (2013.01); *G21K 1/093* (2013.01); *G21K 5/04* (2013.01); *A61N 2005/1087* (2013.01)

(58) Field of Classification Search
CPC .................. A61N 5/1081; A61N 5/01; A61N 2005/1087; G21K 1/093
See application file for complete search history.

(56) References Cited

U.S. PATENT DOCUMENTS

| 5,818,058 A | 10/1998 | Nakanishi et al. |
| 5,993,373 A | 11/1999 | Nonaka et al. |
| 2014/0094643 A1* | 4/2014 | Gall .................. A61N 1/44 600/2 |

FOREIGN PATENT DOCUMENTS

| JP | 9-192244 A | 7/1997 |
| JP | 11-47287 A | 2/1999 |

(Continued)

OTHER PUBLICATIONS

International Search Report dated Jun. 12, 2018 in PCT/JP2018/009686 filed Mar. 13, 2018 (with English translation).

(Continued)

*Primary Examiner* — Eliza W Osenbaugh-Stewart
(74) *Attorney, Agent, or Firm* — Oblon, McClelland, Maier & Neustadt, L.L.P.

(57) ABSTRACT

A rotary irradiation apparatus of an embodiment comprises: a rotating gantry; a superconducting electromagnet being installed in the rotating gantry and forming at least one of a deflecting magnetic field that deflects a trajectory of a charged particle beam and a convergent magnetic field that converges the charged particle beam to guide the charged particle beam to an object to be irradiated; a rotating gantry drive unit that drives/rotates the rotating gantry; and a control device that controls the rotating gantry drive unit to rotate and stop the rotating gantry, while the superconducting electromagnet is being excited and the charged particle beam is not irradiated.

8 Claims, 9 Drawing Sheets

(51) Int. Cl.
G21K 1/093 (2006.01)
G21K 5/04 (2006.01)

(56) References Cited

FOREIGN PATENT DOCUMENTS

| | | |
|---|---|---|
| JP | 2011-72717 A | 4/2011 |
| JP | 2015-97683 A | 5/2015 |
| JP | 2015-208598 A | 11/2015 |
| WO | WO 2016/014422 A1 | 1/2016 |
| WO | WO 2015/045017 A1 | 3/2017 |

OTHER PUBLICATIONS

Written Opinion dated Jun. 12, 2018 in PCT/JP2018/009686 filed Mar. 13, 2018.

* cited by examiner

ROTARY IRRADIATION APPARATUS, ROTARY IRRADIATION METHOD, AND ROTATION RADIOTHERAPY APPARATUS

CROSS-REFERENCE TO RELATED APPLICATIONS

This application is a continuation application of International Application PCT/JP2018/009686 filed on Mar. 13, 2018, the entire content of which is incorporated herein by reference. This application is based upon and claims the benefit of priority from Japanese Patent Application No. 2017-048806, filed on Mar. 14, 2017; the entire content of which is incorporated herein by reference.

FIELD

An embodiment of the present invention relates to a rotary irradiation apparatus, a rotary irradiation method, and a rotation radiotherapy apparatus that irradiate an irradiation subject (target) with a charged particle beam from a desired peripheral angle.

BACKGROUND

Generally, a rotation radiotherapy apparatus is rotated around a patient and irradiates the patient with a charged particle beam which has been accelerated up to high energy by an accelerator such as a synchrotron from a desired peripheral angle. Thus, the rotation radiotherapy apparatus is provided with a rotation frame (hereinafter, referred to as "rotating gantry") configured to rotate around the patient.

The charged particle beam accelerated to high energy by an accelerator such as a synchrotron is guided in a direction toward the rotation center of the rotating gantry. The charged particle beam guided in the rotation center axial direction is once bent in the radially outer direction of the rotating gantry by a beam transport device provided with superconducting electromagnets and then bent once again in the radially inner direction thereof to be guided to a treatment room. The charged particle beam guided to the treatment room is irradiated from an irradiation unit onto the affected part of the patient to be irradiated.

The rotation radiotherapy apparatus can change the rotation angle of the rotating gantry so as to change the irradiation angle of the charged particle beam with respect to the patient. Conventionally, when the irradiation angle is changed, the rotating gantry is rotated without exciting the superconducting electromagnets and is stopped at a desired angle position. Thereafter, the superconducting electromagnets are excited for irradiation of the charged particle beam.

DETAILED DESCRIPTION

In the above-described operation method of the conventional rotation radiotherapy apparatus, the rotating gantry is rotated without exciting the superconducting electromagnets, so that members constituting the superconducting electromagnets may be slightly displaced by gravitational force applied during rotation of the rotating gantry, causing a problem in that the superconducting electromagnets are mechanically quenched at the time of excitation after the stop of rotation of the rotating gantry. This is one of the factors that prevents smooth treatment of the rotation radiotherapy apparatus. The reason for occurrence of the quenching will be specifically described below.

Each of the superconducting electromagnets mainly includes a coil that generates a magnetic field and an electromagnet force support member for supporting electromagnetic force. Typically, the rotating gantry is rotated in a non-excitation state since the charged particle beam does not pass through the superconducting electromagnet. In the non-excitation state, electromagnetic force is not generated in the coils, so that no or little friction force is generated between the electromagnet force support member and the coils.

When acceleration and vibration associated with the rotation of the rotating gantry are applied in this state, slight displacement or slight distortion may occur between the electromagnet force support members and the coils in the superconducting electromagnets. When the superconducting electromagnets are re-excited in this state, elimination of the displacement or distortion causes mechanical disturbance to result in heat generation, which may induce the quenching.

When the superconducting electromagnets are quenched, heat generation occurs, so that it is necessary to stop the operation of the rotation radiotherapy apparatus and to restart after re-cooling of the superconducting electromagnets. Thus, there is nothing for it but to stop treatment by the rotation radiotherapy apparatus, resulting in prolongation of treatment time.

The object of the present embodiment is to provide a rotary irradiation apparatus, a rotary irradiation method, and a rotation radiotherapy apparatus capable of preventing displacement or distortion of the members constituting the superconducting electromagnets associated with the rotation of the rotating gantry.

In order to solve the problems, according to an embodiment, there is presented a rotary irradiation apparatus comprising: a rotating gantry; a superconducting electromagnet being installed in the rotating gantry and forming at least one of a deflecting magnetic field that deflects a trajectory of a charged particle beam and a convergent magnetic field that converges the charged particle beam to guide the charged particle beam to an object to be irradiated; a rotating gantry drive unit that drives/rotates the rotating gantry; and a control device that controls the rotating gantry drive unit to rotate and stop the rotating gantry while the superconducting electromagnet is being excited.

According to an embodiment, there is presented a rotation radiotherapy apparatus having the rotary irradiation apparatus according to the embodiment described above.

According to an embodiment, there is presented a rotary irradiation method that guides a charged particle beam to an object to be irradiated using a superconducting electromagnet installed in a rotating gantry and forms at least one of a deflecting magnetic field that deflects a trajectory of the charged particle beam and a convergent magnetic field that converges the charged particle beam, the method comprising: a step in which a control device controls the superconducting electromagnet to be excited; and a step in which the control device controls a rotating gantry drive unit to rotate and stop the rotating gantry while the superconducting electromagnet is being excited.

Hereinafter, a rotation radiotherapy apparatuses according to embodiments of the present invention will be described with reference to the drawings. In the following embodiments, examples in which rotary irradiation apparatuses are applied to rotation radiotherapy apparatuses will be described.

Entire Configuration of Rotation Radiography Apparatus

Figure 1:
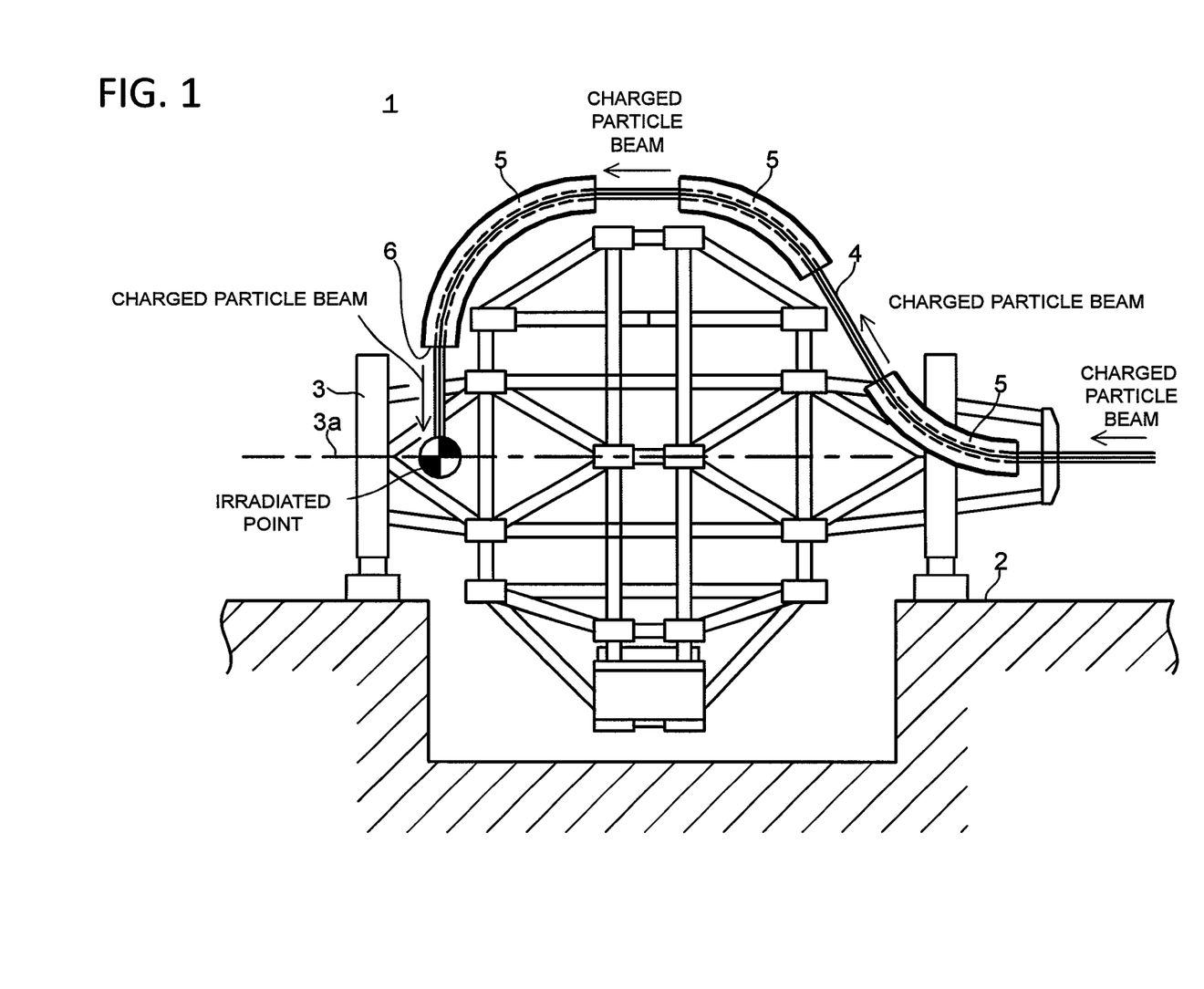
FIG. 1 is a longitudinal cross-sectional view illustrating a rotation radiotherapy apparatus according to an embodiment.
Figure 2:
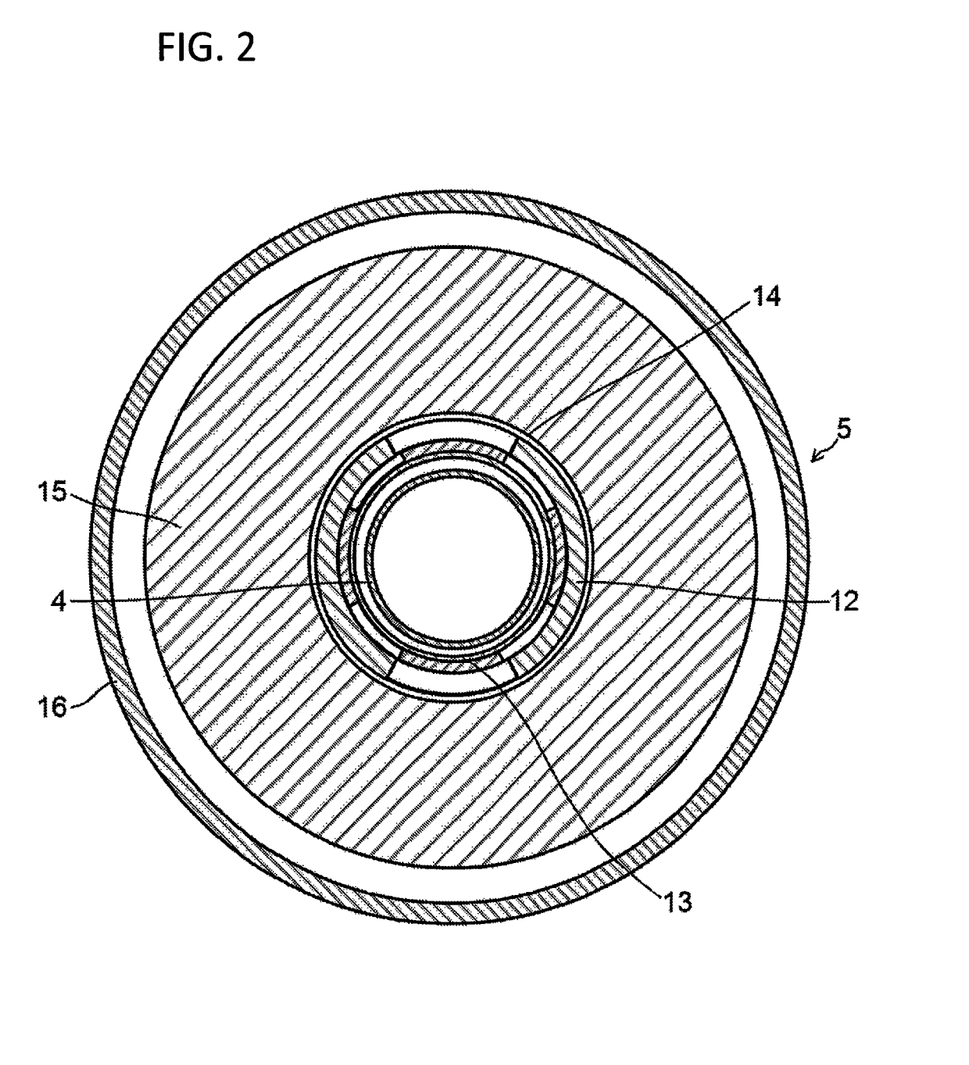
FIG. 2 is a traverse cross-sectional view illustrating a composite superconducting electromagnet illustrated in FIG. 1.

FIG. 1 is a longitudinal cross-sectional view illustrating a rotation radiotherapy apparatus according to an embodiment. FIG. 2 is a traverse cross-sectional view illustrating a composite superconducting electromagnet illustrated in FIG. 1.

First, with reference to FIG. 1, the entire configuration of a rotation radiotherapy apparatus 1 in the present embodiment will be described.

The rotation radiotherapy apparatus 1 illustrated in FIG. 1 is installed in a building 2. The rotation radiotherapy apparatus 1 mainly includes an accelerator (not illustrated) such as a synchrotron, a rotating gantry 3, a beam pipe (vacuum duct) 4, and composite superconducting electromagnets 5.

The rotating gantry 3 is rotated while holding an irradiation unit 6 serving as a terminal of a beam transport path and an exit of a charged particle beam. The rotating gantry 3 is configured to be rotatable around a rotation axis 3a in a desired angle range. Thus, it is possible to irradiate, from a desired direction, the affected part of the patient to be irradiated that is positioned at a location corresponding to the irradiation unit 6 during treatment.

The beam pipe 4 serves as a beam transport path having its inside in a vacuum state and guiding the charged particle beam accelerated by the accelerator to the patient's affected part.

Each of the composite superconducting electromagnets 5 has, at the outer side of the beam pipe 4, a dipole coil 12 and a quadrupole coil 13 which are concentrically disposed, as illustrated in FIG. 2. The dipole coil 12 is a beam deflecting coil that deflects the charged particle beam. The quadrupole coil 13 is a beam converging coil that converges the charged particle beam. That is, each of the composite superconducting electromagnets 5 simultaneously forms two magnetic fields of a deflecting magnetic field (dipole magnetic field) and a convergent magnetic field (quadrupole magnetic field) as a superposition synthetic magnetic field so as to control a beam trajectory of the charged particle beam.

The convergent magnetic field formed simultaneously with the deflecting magnetic field is controlled so as to forcibly suppress a diffusion component that is directed away from the trajectory center (beam traveling direction) of the charged particle beam passing in the beam pipe 4 and thereby to enhance the directivity of the charged particle beam from the time when the charged particle beam enters the rotating gantry 3 until the time when it is emitted from the irradiation unit 6. Such control of the deflecting magnetic field is also achieved by the arrangement of the composite superconducting electromagnets 5.

In the present embodiment, three composite superconducting electromagnets 5 are provided inside the rotating gantry 3 so as to be spaced apart from one another by predetermined distances. In each composite superconducting electromagnet 5, an electromagnetic force support member 15 serving also as an iron yoke is disposed radially outside the dipole and quadrupole coils 12 and 13 through a spacer 14 in a concentric manner therewith. Further, a vacuum vessel 16 is provided radially outside the electromagnetic force support member 15 in a concentric manner therewith.

The composite superconducting electromagnets 5 have active shield coils so as to reduce a leakage magnetic field. The composite superconducting electromagnets 5 have no influence of the magnetic field on the structure of the rotating gantry 3 or not-shown measurement devices such as a monitor and has a leakage magnetic field reduced with respect to the irradiation unit 6. Thus, the composite superconducting electromagnets 5 have a structure having no influence of the magnetic field on the patient or medical treatment equipment.

Operation of Rotation Radiotherapy Apparatus

A charged particle beam such as a carbon ion beam or a proton beam is accelerated up to high energy of several hundred MeV by an accelerator (not illustrated) such as a synchrotron and introduced to the rotation radiotherapy apparatus 1 through the beam line. The charged particle beam, which is composed of a heavy particle beam or a proton beam, passes in the beam pipe 4, which maintains a vacuum. After that, the trajectory of the charged particle beam is bent three times by deflecting magnetic fields (dipole magnetic fields) of the composite superconducting electromagnets 5. Finally, the charged particle beam is emitted from the irradiation unit 6 to irradiate the affected part (irradiation point) of the patient to be irradiated in a perpendicular direction.

The quadrupole magnetic field of each composite superconducting electromagnet 5 prevents diffusion of the charged particle beam as described above to allow a high precision charged particle beam to be supplied to the irradiation unit 6.

System Configuration

Figure 3:
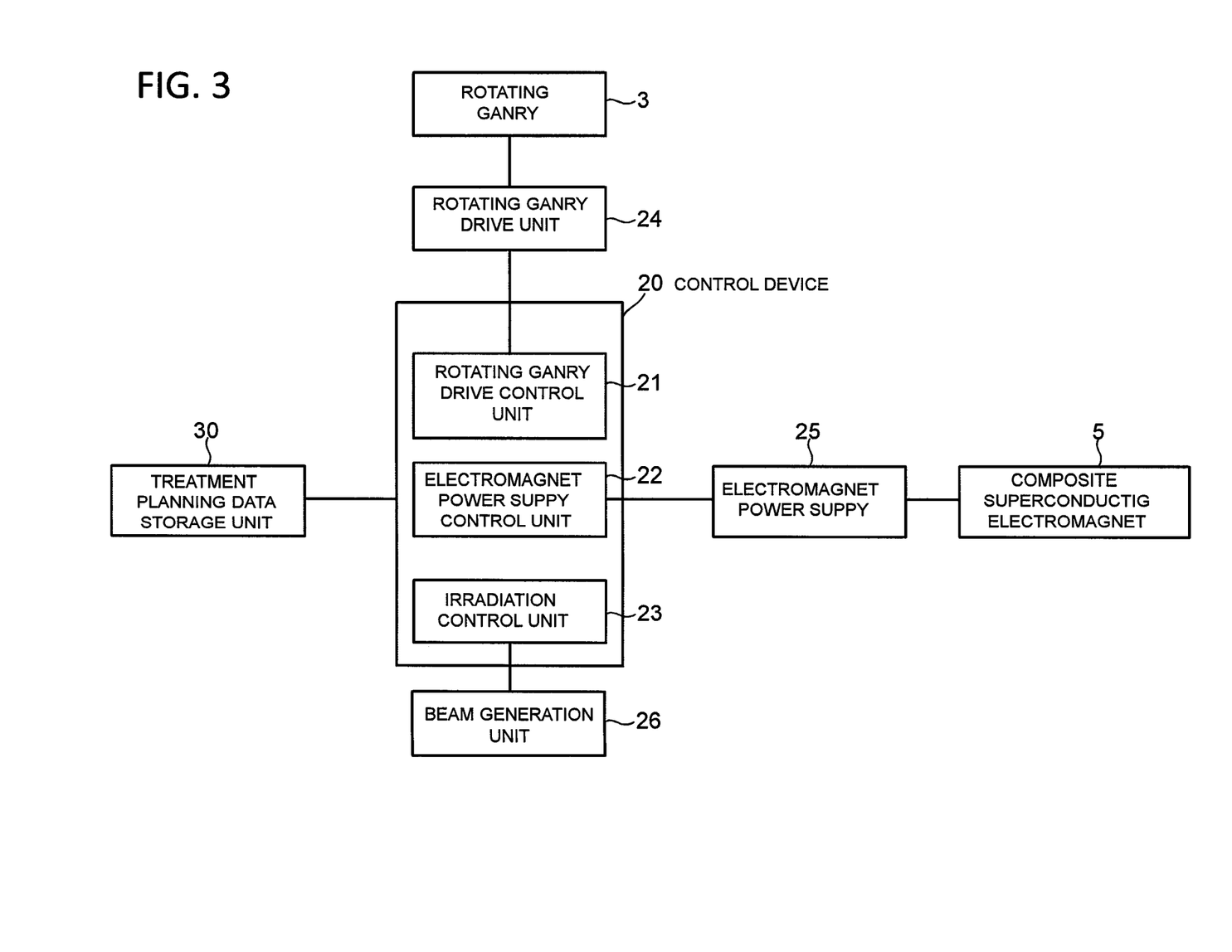
FIG. 3 is a block diagram illustrating the system configuration of the rotation radiotherapy apparatus according to the embodiment.

FIG. 3 is a block diagram illustrating the system configuration of the rotation radiotherapy apparatus according to the embodiment.

As illustrated in FIG. 3, a control device 20 is constituted by a computer resource such as a microcomputer. In the control device 20, a CPU (Central Processing Unit) reads out a processing program and various data stored in a not-shown recording medium such as a ROM (Read Only Memory) or a hard disk drive, expands them in a main memory, and sequentially executes the expanded processing program, whereby a method corresponding the program is executed. The number of microcomputers constituting the control device 20 may be one or more.

The control device 20 has, as functional elements realized by the CPU executing the processing program, a rotating gantry drive control unit 21, an electromagnet power supply control unit 22, and an irradiation control unit 23. The above elements constituting the control device 20 may be implemented not only in software, but may be in part or in whole in hardware which is combined with a logic circuit, an analog circuit, or the like.

The rotating gantry drive control unit 21 is connected to a rotating gantry drive unit 24 that drives the rotating gantry 3. The rotating gantry drive control unit 21 controls the rotating gantry drive unit 24 to thereby control ON/OFF timing of the rotating gantry 3. Thus, the position and direction of the irradiation unit 6 with respect to the affected part of the patient to be irradiated are controlled.

The electromagnet power supply control unit 22 is connected to an electromagnet power supply 25 through signal lines. The electromagnet power supply 25 is connected to the composite superconducting electromagnets 5 through signal lines. The electromagnet power supply control unit 22 controls the electromagnet power supply 25 to thereby control ON/OFF of the composite superconducting electromagnets 5 and to control the excitation amount (exciting current) of the composite superconducting electromagnets 5 and excitation timing thereof by the excitation amount.

Although the electromagnet power supply control unit 22, the electromagnet power supply 25, and the composite superconducting electromagnets 5 may be separately formed in the present embodiment, all of them may be integrally formed. Alternatively, only the electromagnet power supply control unit 22 and the electromagnet power supply 25 may be integrally formed, or only the electromagnet power supply 25 and the composite superconducting electromagnets 5 may be integrally formed.

The irradiation control unit 23 is connected to a beam generation unit 26. The beam generation unit 26 generates particles of carbon ion, proton, or the like and generates a charged particle beam by accelerating, by an accelerator, such as a synchrotron, the particles up to energy high enough to allow them to reach deeply the affected part.

The irradiation control unit 23 performs ON/OFF control of emission of the charged particle beam generated by the beam generation unit 26. Specifically, the control device 20 acquires a dose full signal from, e.g., a not-shown dose monitor to output a beam emission permission signal. The dose monitor monitors the dose irradiated to the affected part. The irradiation control unit 23 controls ON/OFF of emission of the charged particle beam based on the beam emission permission signal.

A treatment planning data storage unit (data storage unit) 30 is constituted by a storage medium such as a hard disk drive. In the treatment planning data storage unit 30, specifications required to determine the irradiation timing of the charged particle beam, the excitation amount and excitation timing of the composite superconducting electromagnets 5, the ON/OFF timing of rotation of the rotating gantry 3, and the like are stored in the processing order in a data file called, e.g., a pattern file. The stored specifications are output to the control device 20 before the start of treatment irradiation.

The control device 20 controls the rotating gantry drive control unit 21, electromagnet power supply control unit 22, and irradiation control unit 23, on the basis of the input data.

System Operation

Figure 4:
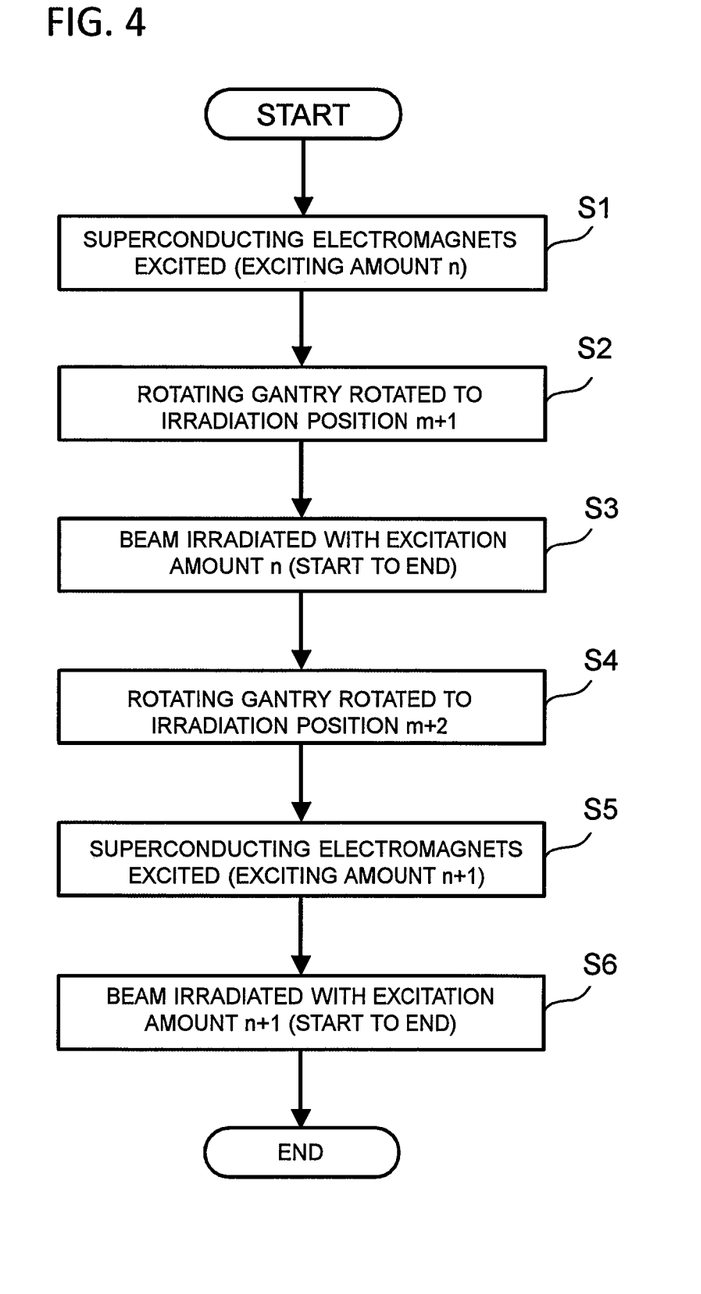
FIG. 4 is a flowchart illustrating the control sequence of the control device of FIG. 3.
Figure 5:
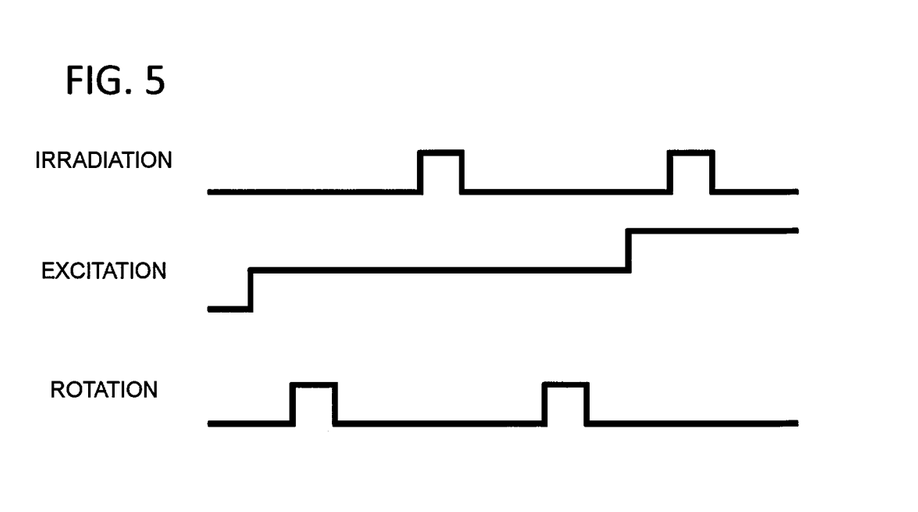
FIG. 5 is a timing chart illustrating the irradiation timing of the beam generation unit, excitation timing of the composite superconducting electromagnets, and timing of the rotation operation of the rotating gantry in the control sequence of FIG. 3.

FIG. 4 is a flowchart illustrating the control sequence of the control device. FIG. 5 is a timing chart illustrating the irradiation timing of the beam generation unit, excitation timing of the composite superconducting electromagnets, and timing of the rotation operation of the rotating gantry in the control sequence of FIG. 3.

Before the start of treatment irradiation, the control device 20 receives in advance, from the treatment planning data storage unit 30, various data including the irradiation timing of the charged particle beam, the excitation amount and excitation timing of the composite superconducting electromagnets 5, the ON/OFF timing of rotation of the rotating gantry 3, and the like.

First, as illustrated in FIGS. 4 and 5, the electromagnet power supply control unit 22 controls the electromagnet power supply 25 to excite the composite superconducting electromagnets 5 with an excitation amount n (step S1). Then, in a state where the composite superconducting electromagnets 5 are not demagnetized, the rotating gantry drive control unit 21 drives/rotates the rotating gantry 3 to another irradiation position (irradiation position m+1) while controlling ON/OFF timing of the rotating gantry drive unit 24 (step S2).

Then, the irradiation control unit 23 controls ON/OFF of emission of the charged particle beam, and makes the beam generation unit 26 emit the charged particle beam with the excitation amount n of the electromagnet power supply 25 while controlling (step S3). With the excitation state maintained, the rotating gantry drive control unit 21 drives/rotates the rotating gantry 3 to still another irradiation position (irradiation position m+2) while controlling ON/OFF timing of the rotating gantry drive unit 24 (step S4).

Further, the electromagnet power supply control unit 22 controls the electromagnet power supply 25 to excite the composite superconducting electromagnets 5 with an excitation amount n+1, which is larger than the excitation amount in step S1 (step S5). The irradiation control unit 23 controls ON/OFF of emission of the charged particle beam, and makes the beam generation unit 26 emit the charged particle beam with the excitation amount n+1 of the electromagnet power supply 25 while controlling (step S6).

Figure 6:
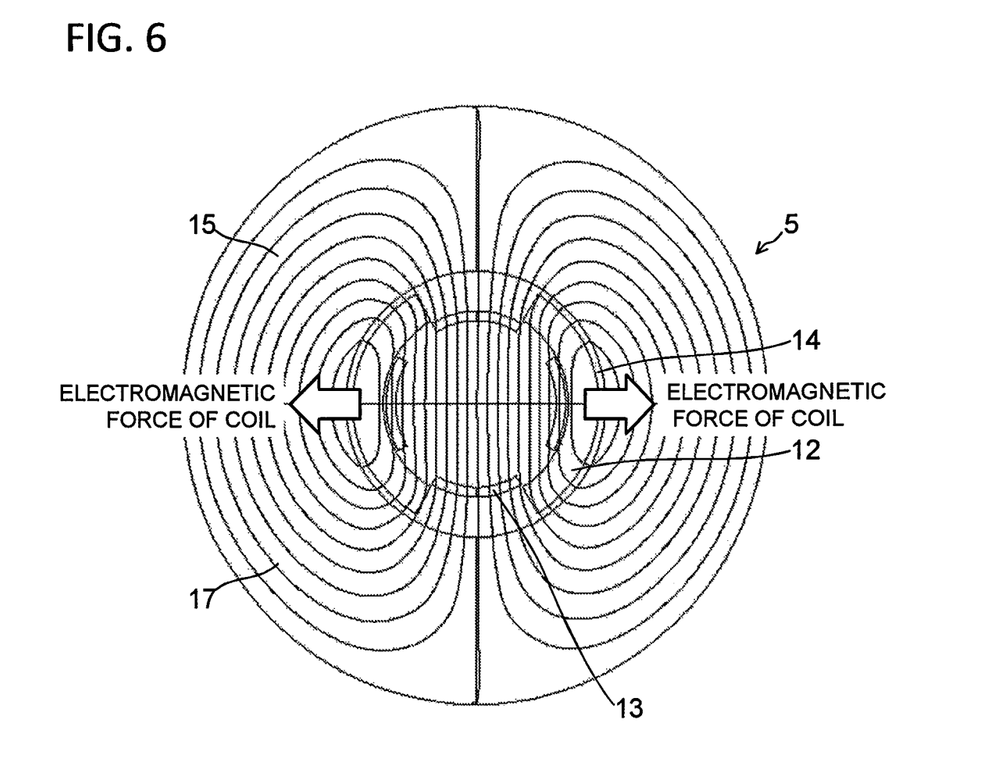
FIG. 6 is an explanatory view illustrating, in a cross section, electromagnetic force acting on the coils of the composite superconducting electromagnet of FIG. 2.

FIG. 6 is an explanatory view illustrating, in a cross section, electromagnetic force acting on the coils of the composite superconducting electromagnet of FIG. 2.

In the present embodiment, the rotating gantry is rotated after excitation of the composite superconducting electromagnets 5, as illustrated in FIGS. 4 and 5. Therefore, as illustrated in FIG. 6, magnetic flux lines 17 act on the dipole coil 12 and quadrupole coil 13 as electromagnetic force. As a result, coil electromagnetic force denoted by the arrows in FIG. 6 acts on the dipole coil 12 and quadrupole coil 13.

This coil electromagnetic force is transmitted to the electromagnetic force support member 15 through the spacer 14 to generate friction force between the dipole and quadrupole coils 12, 13 and the electromagnetic force support member 15. Thus, the dipole and quadrupole coils 12, 13 and the electromagnetic force support member 15 are fixed in position by the friction force, so that even when the rotating gantry 3 is rotated in this state, they are not displaced from each other or distorted, preventing quenching.

Thus, in the present embodiment, the composite superconducting electromagnets 5 are excited while the rotating gantry 3 is rotated, whereby the components inside the composite superconducting electromagnets 5 are restrained in position by the generated electromagnetic force. This prevents displacement of the components inside the composite superconducting electromagnets 5, averting the problem of the superconducting electromagnets being mechanically quenched with the rotation of the rotating gantry 3.

In the present embodiment, the dipole coil 12 and the quadrupole coil 13 are bonded together so as to be integrated. Although the dipole coil 12 and quadrupole coil 13 are disposed on the radially inner side and the radially outer side, respectively, in FIG. 2, the positions thereof may be reversed.

Further, in the present embodiment, the excitation amount of the composite superconducting electromagnets 5 may be any value as long as friction force is generated between the dipole and quadrupole coils 12, 13 and the electromagnetic force support member 15 to fix them in position.

As described above, in the present embodiment, the rotating gantry 3 is rotated after excitation of the composite superconducting electromagnets 5, so that it is possible to prevent occurrence of displacement or distortion, due to the rotation of the rotating gantry 3, of the components inside the composite superconducting electromagnets 5, thereby making it possible to prevent the composite superconducting electromagnets 5 from being mechanically quenched by the rotation of the rotating gantry 3. This eliminates the need to stop the operation of the rotation radiotherapy apparatus 1, resulting in reduction in treatment time.

Further, in the present embodiment, the excitation amount of the composite superconducting electromagnets 5 can be switched in two steps, so that it is possible to complete, in short time, irradiation of a proper dose of the charged particle beam to the affected part of the patient to be irradiated. Although the excitation amount of the composite superconducting electromagnets 5 can be switched in two steps in the present embodiment, the number of switching steps may be three or more. This enables a proper dose of the charged particle beam to be irradiated in a shorter time.

Further, in the present embodiment, the excitation amount of the composite superconducting electromagnet 5 for the next irradiation cycle is set during rotation of the rotating gantry 3, whereby it is possible to save time and trouble for setting the excitation amount at the time of irradiation.

Figure 7:
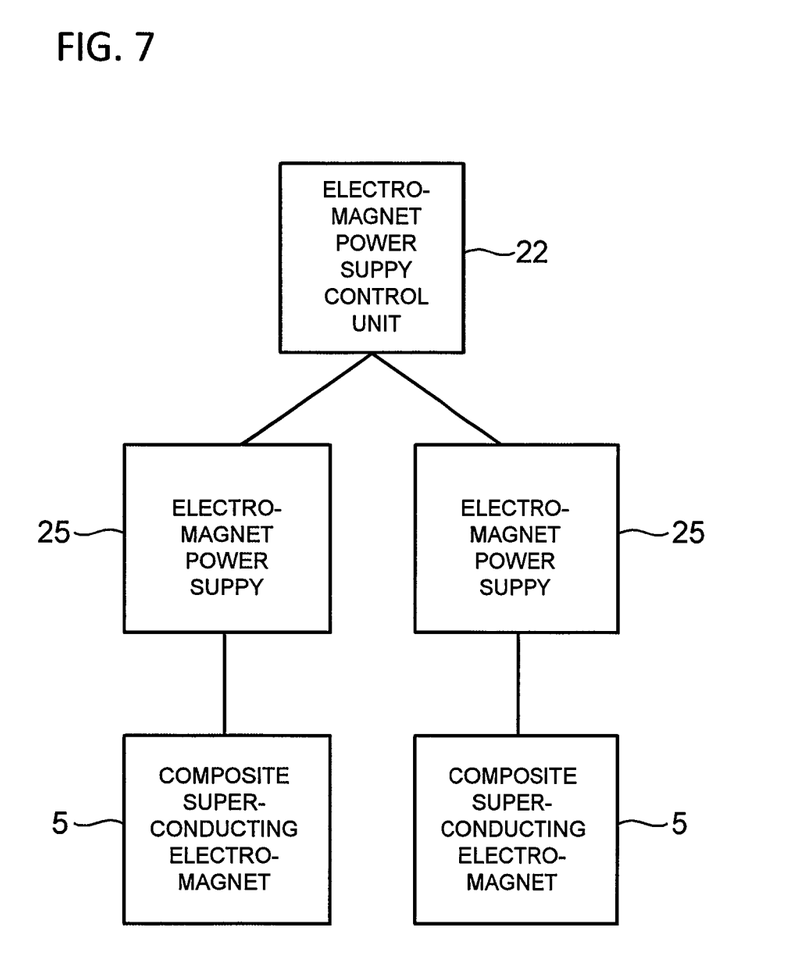
FIG. 7 is a block diagram illustrating another example of the connection configuration of the composite superconducting electromagnets.

Another Example of Connection Configuration of Composite Superconducting Electromagnet FIG. 7 is a block diagram illustrating another example of the connection configuration of the composite superconducting electromagnets 5 of FIG. 3.

In the embodiment illustrated in FIG. 3, the electromagnet power supply control unit 22 is connected with one set of the electromagnet power supply 25 and composite superconducting electromagnet 5, while in FIG. 7, the electromagnet power supply control unit 22 is connected with two sets of the electromagnet power supplies 25 and composite superconducting electromagnets 5.

Thus, the number of the electromagnet power supply control units 22 can be reduced as compared to the embodiment illustrated in FIG. 3, simplifying the configuration.

Although the electromagnet power supply control unit 22 is connected with two sets of the electromagnet power supply 25 and the composite superconducting electromagnet 5 each, in FIG. 7, it may be connected with three sets or more thereof.

Further, although the electromagnet power supplies 25 and the composite superconducting electromagnets 5 are separately formed, they may be formed integrally as in the above embodiment.

Another Example of Control Sequence of Control Device

Figure 8:
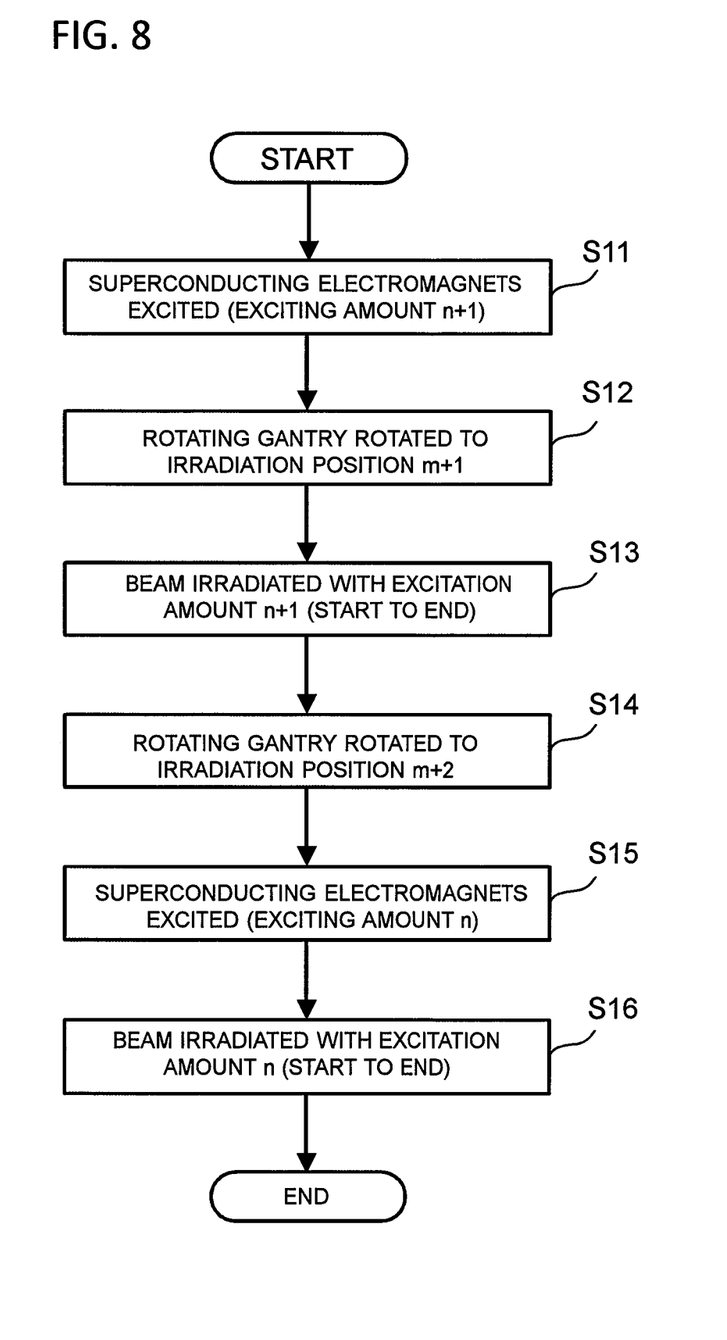
FIG. 8 is a flowchart illustrating another example of the control sequence of the control device according to the embodiment.
Figure 9:
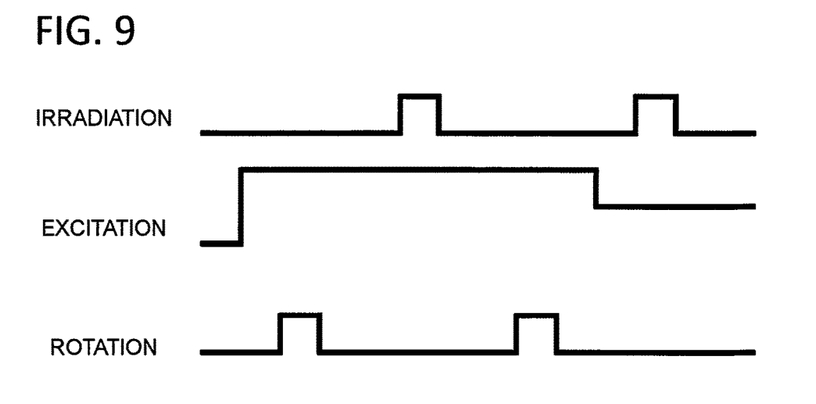
FIG. 9 is a timing chart illustrating another example of the irradiation timing of the beam generation unit, excitation timing of the composite superconducting electromagnets, and timing of the rotation operation of the rotating gantry in the control sequence of FIG. 8.

FIG. 8 is a flowchart illustrating another example of the control sequence of the control device according to the embodiment. FIG. 9 is a timing chart illustrating another example of the irradiation timing of the beam generation unit, excitation timing of the composite superconducting electromagnets, and timing of the rotation operation of the rotating gantry in the control sequence of FIG. 8. Also in this example, various data are output in advance from the treatment planning data storage unit 30 to the control device 20, as in the above embodiments. The same applies to still another example of the control sequence to be described later.

First, as illustrated in FIGS. 8 and 9, the electromagnet power supply control unit 22 controls the electromagnet power supply 25 to excite the composite superconducting electromagnets 5 with an excitation amount n+1 (step S11). Then, in a state where the composite superconducting electromagnets 5 are not demagnetized, the rotating gantry drive control unit 21 drives/rotates the rotating gantry 3 to another irradiation position (irradiation position m+1) while controlling ON/OFF timing of the rotating gantry drive unit 24 (step S12).

Then, the irradiation control unit 23 controls ON/OFF of emission of the charged particle beam, and makes the beam generation unit 26 emit the charged particle beam with the excitation amount n+1 of the electromagnet power supply 25 while controlling (step S13). With the excitation state maintained, the rotating gantry drive control unit 21 drives/rotates the rotating gantry 3 to still another irradiation position (irradiation position m+2) while controlling ON/OFF timing of the rotating gantry drive unit 24 (step S14).

Further, the electromagnet power supply control unit 22 controls the electromagnet power supply 25 to excite the composite superconducting electromagnets 5 with an excitation amount n, which is smaller than the excitation amount in step S11 (step S15). The irradiation control unit 23 controls ON/OFF of emission of the charged particle beam, and makes the beam generation unit 26 emit the charged particle beam with the excitation amount n of the electromagnet power supply 25 while controlling (step S16).

Even when the irradiation timing of charged particle beam, excitation timing and excitation amount of the composite superconducting electromagnets 5, and ON/OFF timing of the rotation operation of the rotating gantry 3 are controlled in the manner as illustrated in FIGS. 8 and 9, the same effects as those in the above embodiments can be obtained.

Still Another Example of Control Sequence of Control Device

Figure 10:
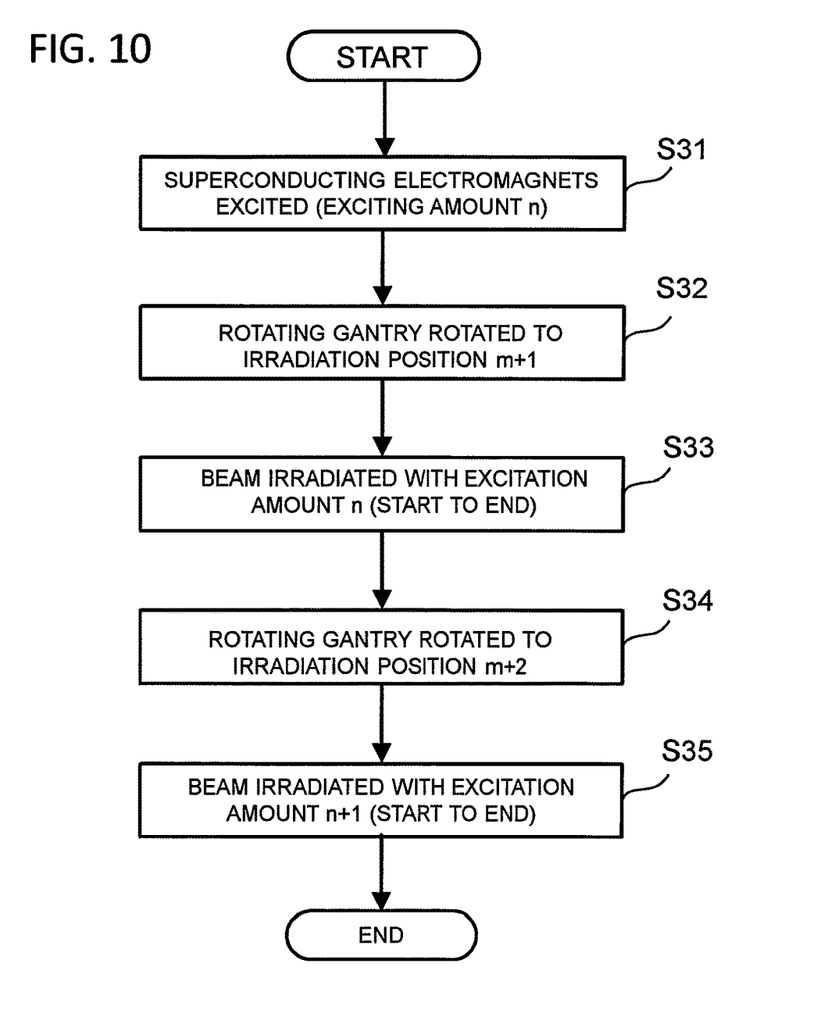
FIG. 10 is a flowchart illustrating still another example of the control sequence of the control device according to an embodiment.
Figure 11:
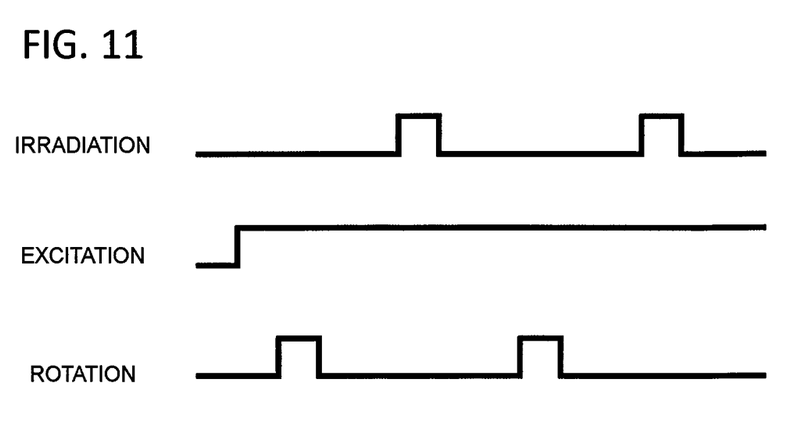
FIG. 11 is a timing chart illustrating still another example of the irradiation timing of the beam generation unit, excitation timing of the composite superconducting electromagnets, and timing of the rotation operation of the rotating gantry in the control sequence of FIG. 10.

FIG. 10 is a flowchart illustrating still another example of the control sequence of the control device according to an embodiment. FIG. 11 is a timing chart illustrating still another example of the irradiation timing of the beam generation unit, excitation timing of the composite superconducting electromagnets, and timing of the rotation operation of the rotating gantry in the control sequence of FIG. 10.

First, as illustrated in FIGS. 10 and 11, the electromagnet power supply control unit 22 controls the electromagnet power supply 25 to excite the composite superconducting electromagnets 5 with an excitation amount n (step S31). Then, in a state where the composite superconducting electromagnets 5 are not demagnetized, the rotating gantry drive control unit 21 drives/rotates the rotating gantry 3 to another irradiation position (irradiation position m+1) while controlling ON/OFF timing of the rotating gantry drive unit 24 (step S32).

Then, the irradiation control unit 23 makes the beam generation unit 26 emit the charged particle beam with the excitation amount n of the electromagnet power supply 25 while controlling ON/OFF of emission of the charged particle beam (step S33). With the excitation state maintained, the rotating gantry drive control unit 21 drives/rotates the rotating gantry 3 to still another irradiation position (irradiation position m+2) while controlling ON/OFF timing of the rotating gantry drive unit 24 (step S34).

Further, with the excitation amount n of the electromagnet power supply 25 maintained, the irradiation control unit 23 makes the beam generation unit 26 emit the charged particle beam with the excitation amount n of the electromagnet power supply 25 while controlling ON/OFF of emission of the charged particle beam (step S35).

Even when the excitation amounts of the composite superconducting electromagnets 5 are controlled constant as illustrated in FIGS. 10 and 11, the same effects as those in the above embodiments can be obtained.

As described above, in the present embodiment, the rotating gantry 3 is rotated after excitation of the composite superconducting electromagnets 5.

Other Embodiments

While certain embodiments of the present invention have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Although the present invention is applied to the rotation radiotherapy apparatus 1 in the above embodiments, any rotary irradiation apparatus that irradiates an object to be irradiated with the charged particle beam from a desired peripheral angle can be applied for various purposes such as physics experiments.

Further, in the above embodiments, both the dipole coil 12 and quadrupole coil 13 are installed; however, when superconducting electromagnets including only the dipole coils 12 or the quadrupole coils 13 are used, the same effects as above can be obtained. Further, the dipole coils 12 and/or the quadrupole coils 13 may each be multipole coils with six or more poles.

What is claimed is:

1. A rotary irradiation apparatus comprising:
a rotating gantry;
a superconducting electromagnet being installed in the rotating gantry and forming at least one of a deflecting magnetic field that deflects a trajectory of a charged particle beam and a convergent magnetic field that converges the charged particle beam to guide the charged particle beam to an object to be irradiated;
a rotating gantry drive unit that drives/rotates the rotating gantry; and
a control device that controls the rotating gantry drive unit to rotate and stop the rotating gantry, while the superconducting electromagnet is being excited and the charged particle beam is not irradiated.

2. The rotary irradiation apparatus according to claim 1, wherein
the control device includes:
an electromagnet power supply control unit that controls excitation timing of the superconducting electromagnet by an electromagnet power supply;
an irradiation control unit that controls ON/OFF of emission of the charged particle beam; and
a rotating gantry drive control unit that controls the rotating gantry drive unit to rotate and stop of the rotating gantry.

3. The rotary irradiation apparatus according to claim 2, further comprising signal lines connecting the superconducting electromagnet, the electromagnet power supply and the electromagnet power supply control unit to one another.

4. The rotary irradiation apparatus according to claim 2, wherein
the electromagnet power supply control unit is configured to switch an exciting amount of the superconducting electromagnet in multiple steps.

5. The rotary irradiation apparatus according to claim 2, wherein
the electromagnet power supply control unit sets excitation amount of the superconducting electromagnet to an excitation amount for a next irradiation cycle.

6. The rotary irradiation apparatus according to claim 1, further comprising a data storage unit storing data of irradiation timing of the charged particle beam, excitation amount and excitation timing of the superconducting electromagnet, and ON/OFF timing of rotation of the rotating gantry, the data storage unit being configured to output data to the control device before irradiation of the charged particle beam starts.

7. A rotation radiotherapy apparatus having the rotary irradiation apparatus according to claim 1.

8. A rotary irradiation method that guides a charged particle beam to an object to be irradiated using a superconducting electromagnet installed in a rotating gantry and forms at least one of a deflecting magnetic field that deflects a trajectory of the charged particle beam and a convergent magnetic field that converges the charged particle beam, the method comprising:
a step in which a control device controls the superconducting electromagnet to be excited; and
a step in which the control device controls a rotating gantry drive unit to rotate and stop the rotating gantry, while the superconducting electromagnet is being excited and the charged particle beam is not irradiated.

* * * * *